US008039027B1

(12) United States Patent  
Guilbert et al.

(10) Patent No.: US 8,039,027 B1
(45) Date of Patent: *Oct. 18, 2011

(54) TREATMENT OF AUTOIMMUNE DISEASES WITH AMERICAN GINSENG EXTRACT

(75) Inventors: Larry Guilbert, Edmonton (CA); Jacqueline Shan, Edmonton (CA); Joanne Totosy De Zepetnek, Edmonton (CA)

(73) Assignee: FX LIFE Sciences AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/659,537

(22) PCT Filed: Feb. 25, 2000

(86) PCT No.: PCT/US00/02523
§ 371 (c)(1),
(2), (4) Date: Feb. 6, 2007

(87) PCT Pub. No.: WO00/50054
PCT Pub. Date: Aug. 31, 2000

Related U.S. Application Data

(60) Provisional application No. 60/121,962, filed on Feb. 25, 1999.

(51) Int. Cl.
*A61K 36/894* (2006.01)
*A61K 36/00* (2006.01)
(52) U.S. Cl. .................................. 424/773; 424/725
(58) Field of Classification Search .................. None
See application file for complete search history.

(56) References Cited

U.S. PATENT DOCUMENTS 5,071,839 A 12/1991 Liu
7,186,423 B2 * 3/2007 Shan et al. ............. 424/728

FOREIGN PATENT DOCUMENTS

| CN | 1097605 | 1/1995 |
| CN | 1205880 | 1/1999 |
| JP | 61018722 | 1/1986 |
| JP | 61209599 | 9/1986 |
| JP | 02045501 | * 2/1990 |
| JP | 02067301 | 3/1990 |

OTHER PUBLICATIONS

British Journal of Rheumatology ; Grees Report: Recommendations for the Registration of Drugs Used in the Treatment of Rheumatoid Arthritis; Feb. 1998: 37, pp. 211-215.*
Choo et al.: Histone Deacetylase Inhibitors; New Hope for Rheumatoid Arthritis?; Current Pharmaceutical Design, 2008, 14, 803-820.*
Feldmann, M : Development of Anti-TNF Therapy for Rheumatoid Arthritis; Nature Reviews Immunology 2, (May 2002), pp. 364-371.*
Mount et al.: Rheumatoid Arthritis Market; Nature Reviews Drug Discovery: vol. 4 (Jan. 2005) pp. 11-12.*
Smolen et al.: Therapeutic Strategies for Rheumatoid Arthritis; Nature Reviews Drug Discovery; vol. 2 (Jun. 2003), pp. 473-488.*

(Continued)

*Primary Examiner* — Patricia Leith
(74) *Attorney, Agent, or Firm* — Prout International IP, LLC

(57) ABSTRACT

Use of ginseng extracts designated CVT-E002, $PQ_2$, $PQ_2A$, $PQ_2B$, $PQ_2C$, $PQ_2D$, and $PQ_{223}$ in the preparation of a pharmaceutical composition suitable for treating an autoimmune disease.

1 Claim, 9 Drawing Sheets

OTHER PUBLICATIONS

Soeken et al. Herbal Medicines for the Treatement of Rheumatoid Arthritis: A Systematic Review: Rheumatology; May 2003, 42, 5, pp. 652-659.*

Phillipson, J. New Drugs From Nature—It Could Be Yew; Phytotherapy Research 13 (1999) pp. 2-8.*

Revilla et al. Comparison of Several Procedures Used for the Extraction of Anthocynains From Red Grapes; J. Agric. Food Chem. 1998, 46, pp. 4592-4597.*

International Search Report from application Serial No. PCT/US00/02523.

Breedveld, F.C. et al., Arthritis & Rheumatism vol. 54, No. 1, Jan. 2006, pp. 26-37.

Froelich, C.J. et al., The Journal of Immunology, vol. 151, 7161-7171, No. 12, Dec. 15, 1993.

Hro 'Bjartsson, A. et al., Journal of Internal Medicine 2004; 256: 91-100.

Milner, J.M. et al., Arthritis & Rheumatism, vol. 58, No. 12, Dec. 2008, pp. 3644-3656.

Ronday, H.K. et al., Rheumatology 2001 40: 55-61.

Spaeny-Dekking, E.H.A. et al., The Journal of Immunology, 1998;160;3610-3616.

Tak P.P. et al, Arthritis & Rheumatism, vol. 37 No. 12, Dec. 1994, pp. 1735-1743.

Van Den Berg, W.B., Springer Semin Immunopathol (1998) 20 : 149-164.

* cited by examiner

TREATMENT OF AUTOIMMUNE DISEASES WITH AMERICAN GINSENG EXTRACT

CROSS REFERENCE TO RELATED APPLICATION

This application is a 35 USC §371 National Phase Entry Application from PCT/US00/02523, filed Feb. 25, 2000, and designating the United States, which claims the benefit of U.S. Provisional 60/121,962, filed Feb. 25, 1999.

FIELD OF INVENTION

This invention relates to the use of an American ginseng extract as a therapeutic targeted at autoimmune diseases, such as Crohn's disease (a debilitating inflammatory bowel disease), rheumatoid arthritis, Multiple Sclerosis and autoimmune diabetes (IDDM).

BACKGROUND OF THE INVENTION

Acquired immune responses are initiated by antigen presentation by antigen presenting cells (APC) and are regulated by T helper (TH) lymphocytes. TH1 cells are induced to develop by APC production of IL-12, produce IFNγ and IL-2 and are necessary for acquired cell-mediated responses. TH2 cells are thought to develop by APC production of IL-10 or PGE2, produce IL-4, IL-5, IL-6 and IL-10 and are necessary for acquired antibody immune responses. TNFα is produced by both TH1 and TH2 cells, although the largest source are macrophages, and appears to have an important role in delayed-type hypersensitivity (DTH) responses, an arm of cell-mediated immunity. Its production and effect in cell-mediated immunity is largely a function of the concomitant presence of IFNγ.

Antigen-specific immune responses in adults are thought to be almost entirely mediated by memory cells. Every arm of the adaptive immune system has associated memory cells: antibody-specific B lymphocytes, CTL and T helper lymphocytes that are essential to the development of antibody production and CTL activation. Memory cell-based responses are faster and larger than naïve responses (e.g., a strong response in five days compared with a weak response in ten days).

The effect of patient treatment on acquired immune responses are conveniently evaluated in an in vitro culture model of peripheral blood leukocytes (PBL). Treatment is given to a randomized population, blood is taken before and after treatment and antigen-specific immune responses measured in PBL cultured in the presence and absence of a memory antigen. The memory antigens chosen in the present invention were three live influenza viruses that the patient population would almost surely have encountered in the past two years. The inventors chose as indicators of immune response production of the cytokines IFNγ, IL-12, IL-10 and TNFα, plus production of the cytotoxic T lymphocyte (CTL) and natural killer (NK) cell granule product GrB, a cysteine protease that initiates apoptosis in killer cell targets. IFNγ, IL-2, IL-12 and GrB are measures of cell-mediated immune responses, while IL-10 is a measure of antibody-mediated immune responses. TNFα participates in cell-mediated immune responses but is more a measure of the innate defense (mostly macrophage) component of immune responses.

Many autoimmune diseases involve aberrant acquired cell-mediated immune responses to self antigens. Examples are Crohn's disease (a debilitating inflammatory bowel disease), the early stages of rheumatoid arthritis, Multiple Sclerosis and autoimmune diabetes (IDDM). In general, any treatment or condition that increases cell-mediated immune responses induces the flare of disease, while conditions suppressing cell-mediated immunity alleviate disease. For example, symptoms of rheumatoid arthritis are reduced by pregnancy, a condition that mutes cell-mediated immune responses. The symptoms flare again after delivery, when the immune system is thought to rebound toward its original balance of cell- and antibody-mediated immunity.

SUMMARY OF THE INVENTION

The present invention is directed to the use of an American ginseng extract as a treatment for autoimmune diseases such as those listed above. Preferably, the American ginseng extract is rich in total carbohydrates, especially polysaccharides and oligosaccharides. For the purposes of this application the term "extract rich in total carbohydrates" is defined as an extract containing at least 20%, at least 30%, at least 40%, at least 50%, at least 60%, at least 70%, at least 80% or at least 90% total carbohydrates, especially about 40% or more, most preferably about 60% or more total carbohydrates. Preferably, at least 50%, at least 60%, at least 70%, at least 80%, and most preferably at least 90% of the total carbohydrates are in the form of polysaccharides and oligosaccharides. Preferred extracts in accordance with the invention are described in PCT/US98/25724, filed Dec. 12, 1998, hereby incorporated by reference.

DETAILED DESCRIPTION OF THE INVENTION

Figure 1:
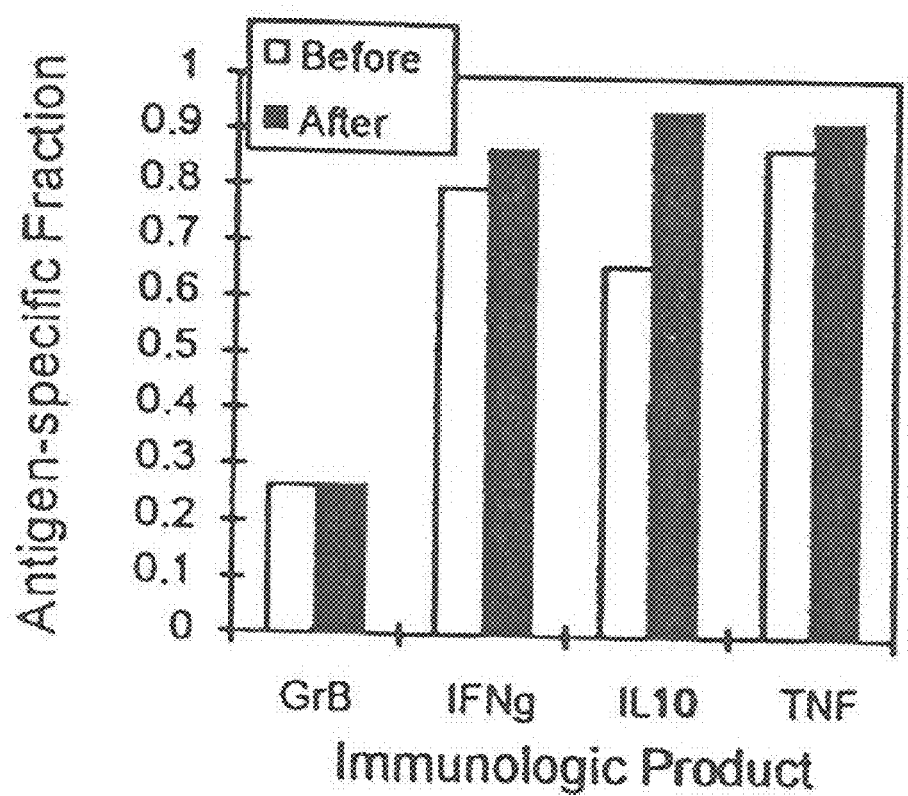
FIG. 1 shows the results of fraction [F=(V−W)/V] for pooled groups (treatment and control groups combined) for four products (GrB, IFN-γ, IL10 and TNF-α) split into start and end subgroups, where (F) is the fraction of production in the presence of virus (V) minus production without virus (W) divided by production in the presence of virus, in order to estimate antigen-dependent production of cytokines or GrB.
Figures 2A, 2B:
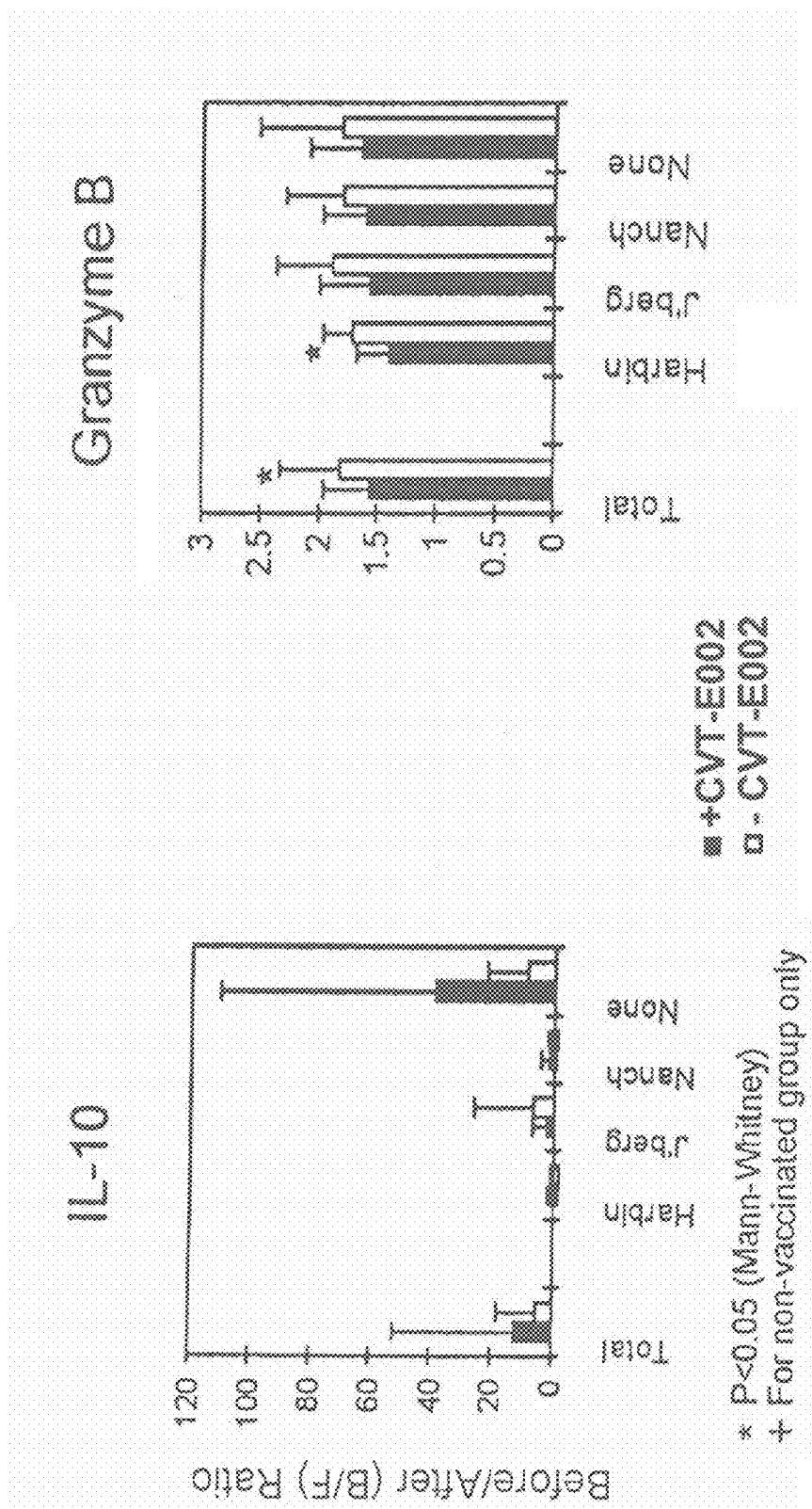
FIGS. 2A-2F show the B/A ratios with and without taking the extract of the invention for all culture protocols (everything pooled="Total") and for each of the antigens and for the control (="None").
Figure 2D:
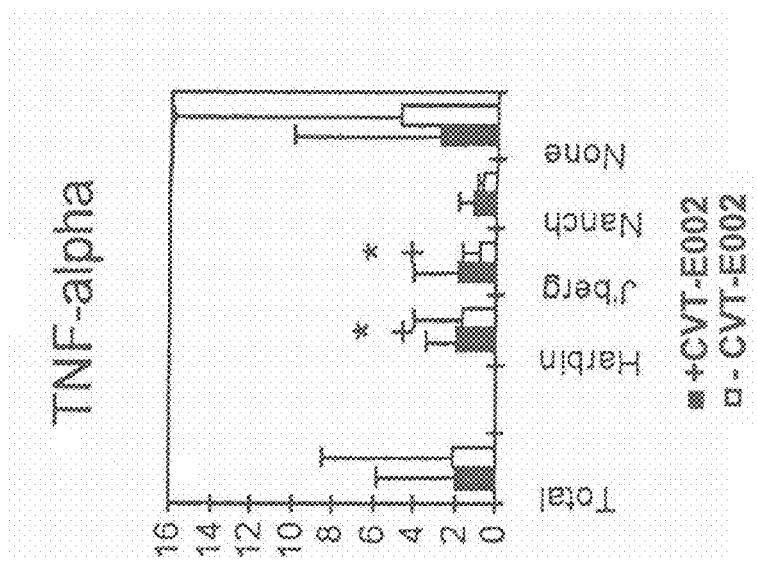
Figure 2C:
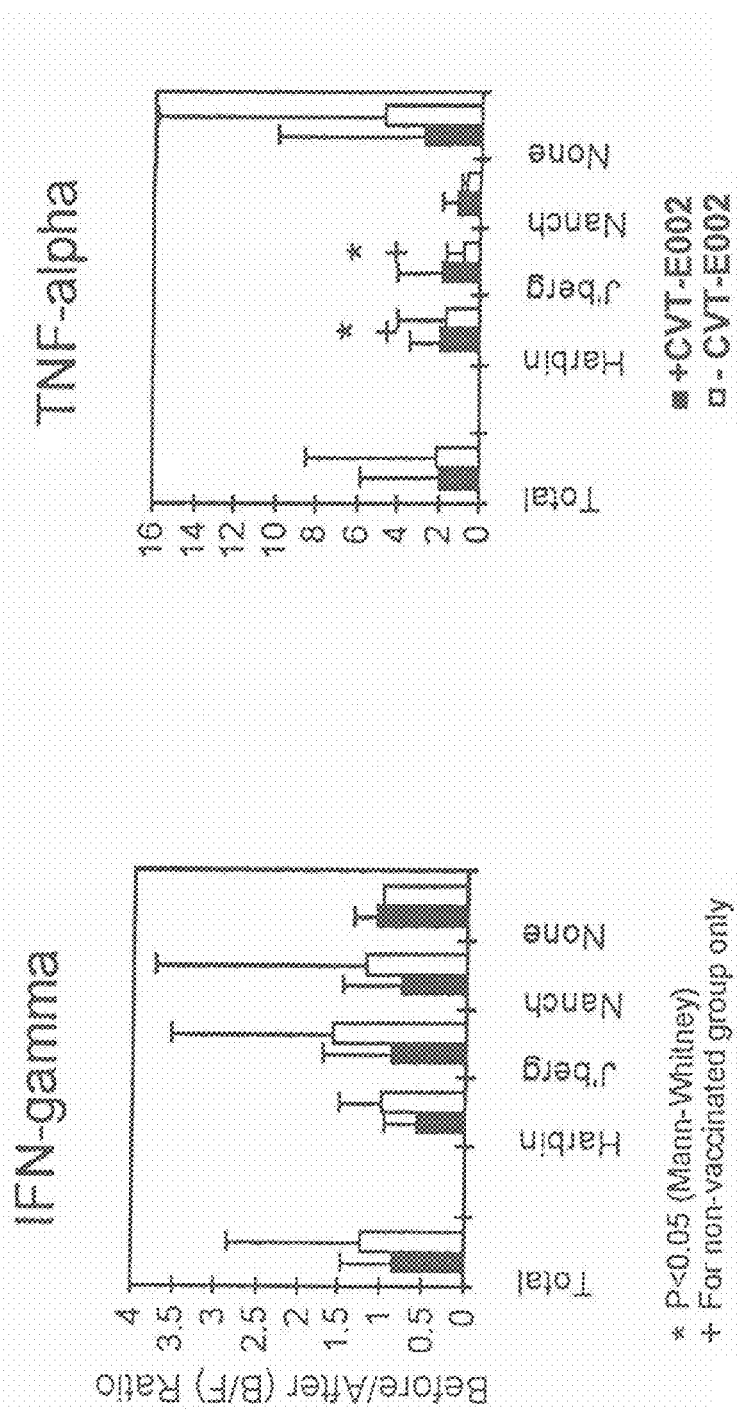
Figures 2E, 2F:
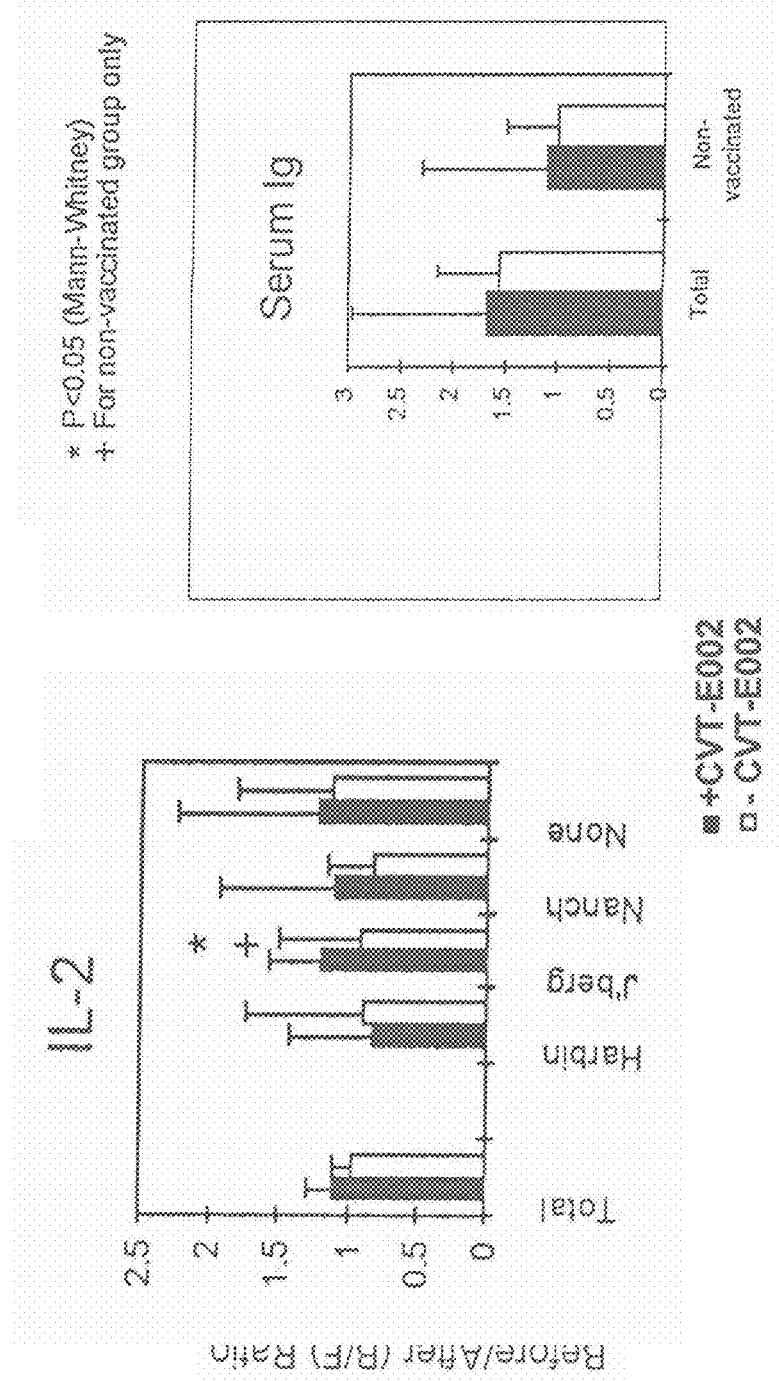
Figure 3A:
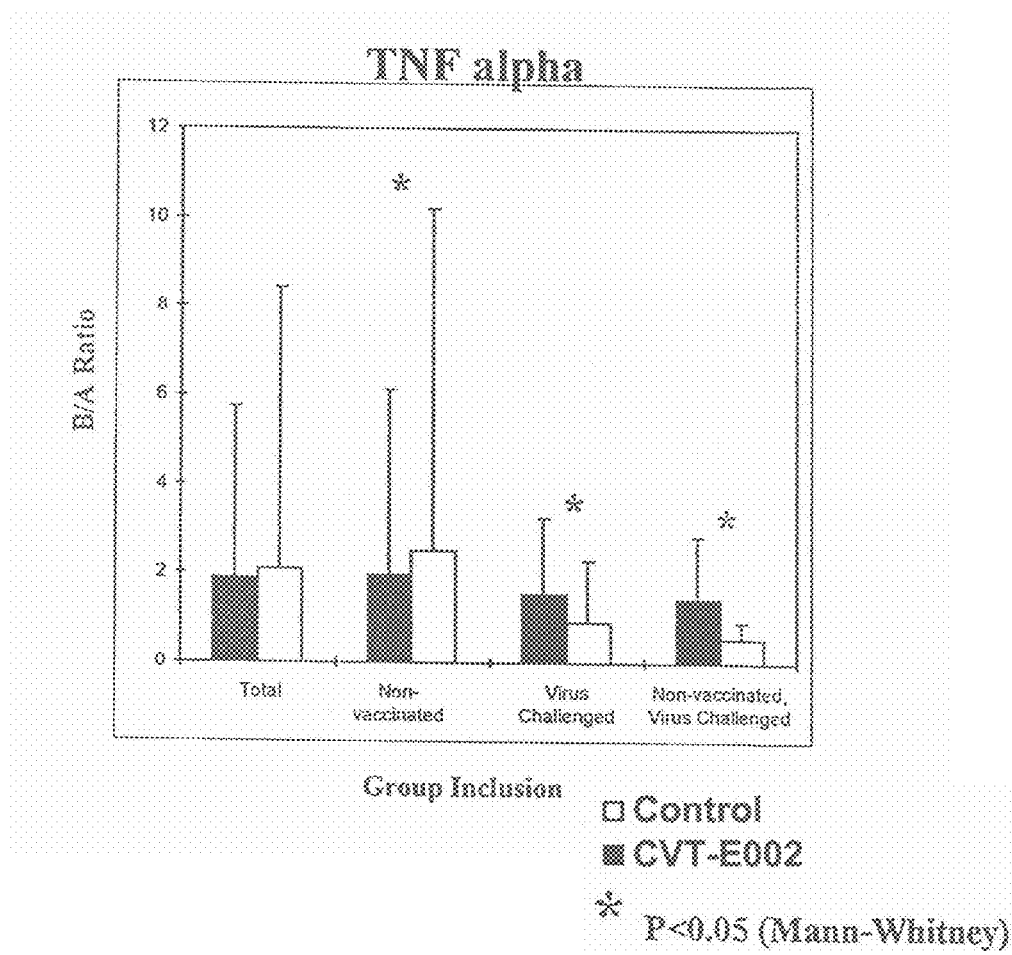
FIGS. 3A-3E compare the B/A ratios for paired -CVT-E002 and +CVT-E002 groups for pooled cultures (="Total"), vaccinated removed, no antigen removed, and both no antigen and vaccinated removed for visual comparison to the Mann-Whitney analysis shown in Table 4.
Figure 3B:
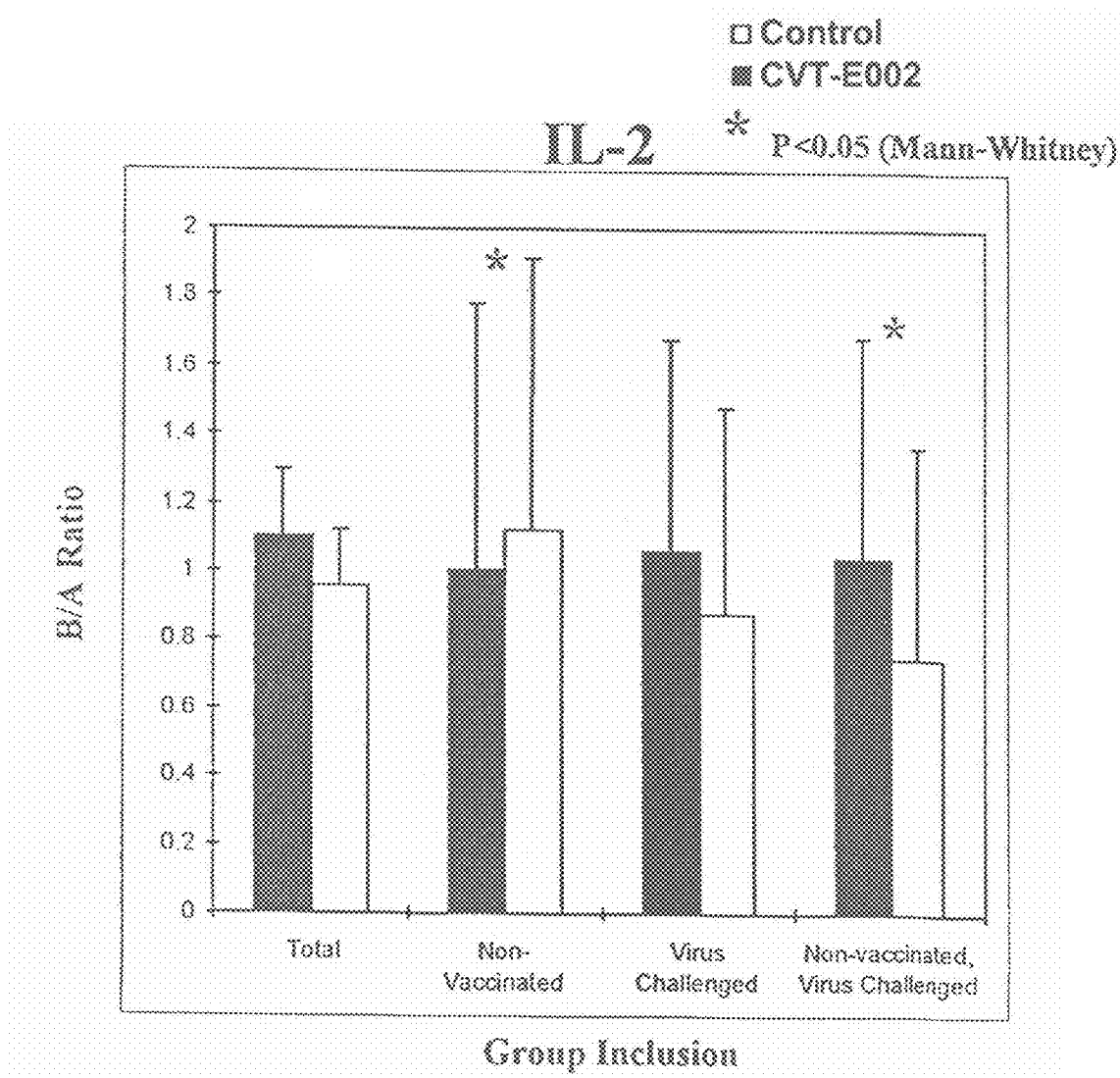
Figure 3C:
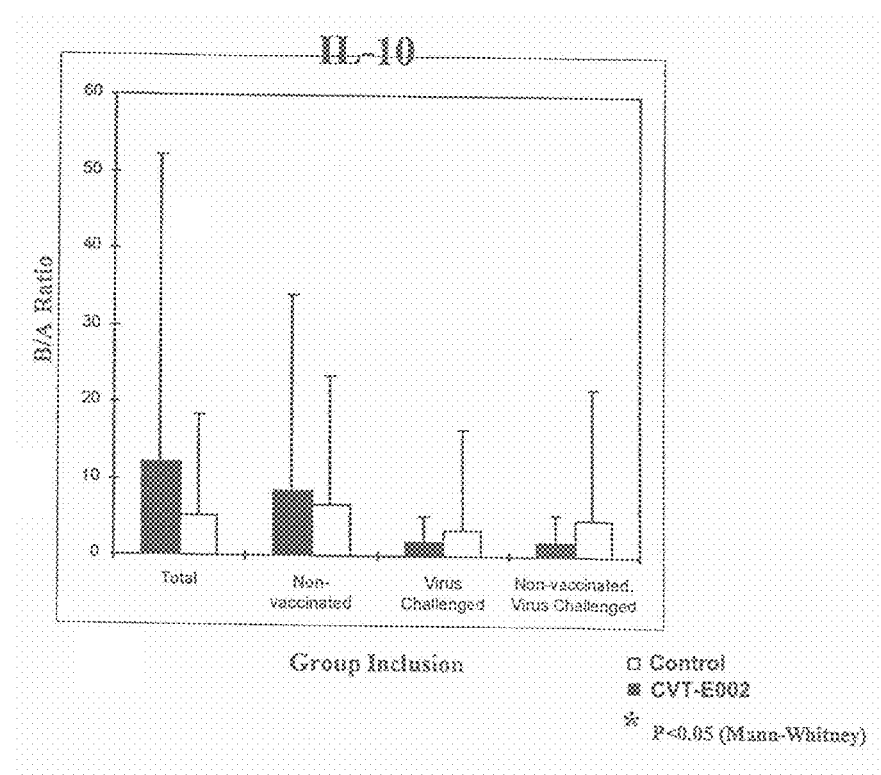
Figure 3D:
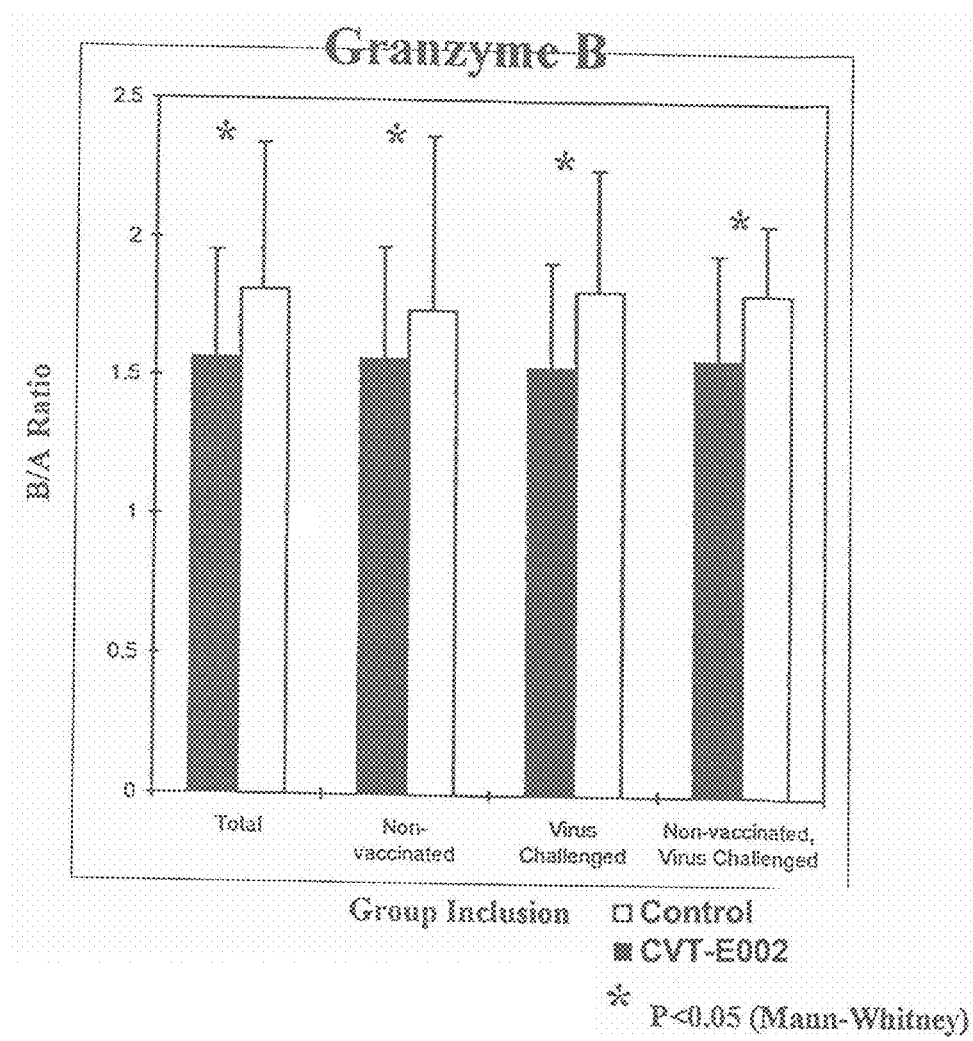
Figure 3E:
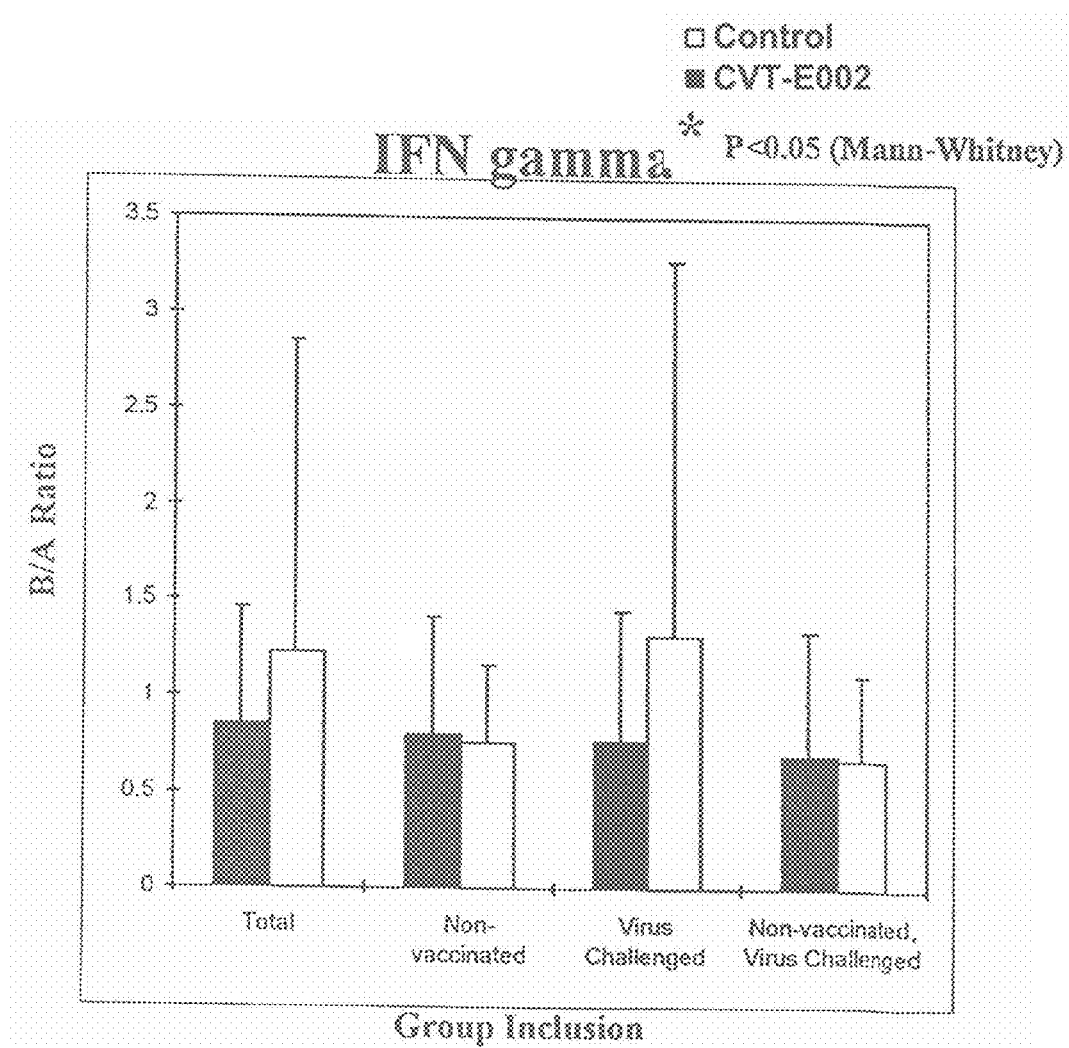

The present inventors have found that an American ginseng extract, preferably an extract containing about 40% or more, most preferably about 60% or more total carbohydrates, especially at least 80%, most preferably at least 90% of the total carbohydrates being in the form of polysaccharides and oligosaccharides, causes an shift of acquired immune responses from cell-mediated immune response to antibody mediated response, i.e., decreasing cell-mediated immune response and increasing antibody-mediated response. This result is indicative of the suitability of the American ginseng extract as a treatment for autoimmune diseases.

Unless otherwise indicated, the percentages expressed herein are in terms of weight %.

Generally, an American ginseng extract in accordance with the invention may be prepared from ginseng leaves and/or roots (preferably roots), in a variety of ways known in the art (see, for example, Oshima et al. *J. Nat. Prod.*, March-April 1987, pp. 188-190; Shoji, J. *Chemistry of Ginseng*; in *Yakuyoninjin* (*Recent Studies on Ginseng*, Tokyo, Kyoritsu Publishing Co., 1981, p. 10), and normally yields 10-40% by weight of the ginseng plant.

The production of the preferred ginseng extracts according to the invention is disclosed in PCT/US98/25724. By following the general methods disclosed therein, one of skill in the art can prepared preferred ginseng extracts designated CVT-E002, $PQ_2$, $PQ_2A$, $PQ_2B$, $PQ_2C$, $PQ_2D$ and $PQ_{223}$.

Process of Preparing Ginseng Fraction CVT-E002

A process of preparing ginseng fraction CVT-E002 comprises:

combining American ginseng with a first solvent comprising an alcohol in a proportion of about 7-9 ml of first solvent per gram of ginseng and heating the resulting solution at a temperature of about 80-100° C. for a time period of about 2-4 hours, to produce a first ginseng solution;

thereafter separating the first ginseng solution to produce an alcohol ginseng solution and a first ginseng residue;

thereafter combining the first ginseng residue with water in a proportion of about 7-9 ml of water per gram of ginseng residue and heating the ginseng residue solution at a temperature of about 80-100° C. for a time period of about 2-4 hours, to produce a ginseng residue solution;

thereafter separating the ginseng residue solution to produce a second ginseng residue and an aqueous extract solution containing a ginseng extract; and drying or concentrating the aqueous extract solution to produce ginseng fraction CVT-E002.

Preferably, CVT-E002 has a total carbohydrate content of about 60% or more, more preferably about 60% to about 70%. Preferably, $PQ_2$ has a total carbohydrate content of about 40% or more, more preferably about 43% to about 53%. Preferably, $PQ_{223}$ has a total carbohydrate content of about 75% or more, more preferably about 78% to about 86%. According to Example 5 disclosed in PCT/US98/25724, several batches of these preferred extracts were obtained, and the total carbohydrate composition (as determined by the phenol-sulfuric method of Dubois et al., *Anal. Chem.* 28: 350-356 (1956)) and the total protein composition (as determined by the method disclosed in Lowry et al., *J. Biol. Chem.* 193: 265-275 (1951)) were measured. For these extracts, the following information was revealed:

TABLE 1

Comparison of Protein and Carbohydrate Content

| Sample | Protein (wt %) | Carbohydrate (wt %) |
| --- | --- | --- |
| E002-1 | 9.32 | 66.4 |
| E002-2 | 7.38 | 69.9 |
| E002-5 | 8.31 | 60 |
| $PQ_2$-24 | 5.6 | 52.6 |
| $PQ_2$-25 | 5.4 | 46.8 |
| $PQ_2$-27 | 5.3 | 43.6 |
| $PQ_{223}$-7 | 5.8 | 78.0 |
| $PQ_{223}$-8 | 2.8 | 81.0 |
| $PQ_{223}$-9 | 2.9 | 85.2 |

Since the total carbohydrate content of these extracts mainly represented polysaccharides and oligosaccharides, the molar ratios of monosaccharides for certain fractions were determined in Example 6 of PCT/US98/25724. The following monosaccharide compositions were obtained:

TABLE 2

Monosaccharide Composition (% in molar)

| Sample | Rhamnose | Galacturonic Acid | Glucose | Galactose | Arabinose |
| --- | --- | --- | --- | --- | --- |
| E002-1 | 2.8 | 17.9 | 53 | 13.3 | 13 |
| E002-2 | 1 | 13.1 | 56.7 | 12.7 | 15.2 |
| E002-3 | 2.9 | 20.4 | 42.1 | 16.5 | 16.3 |
| $PQ_2$-22 | 3.6 | 45.1 | 15.4 | 19.8 | 16.2 |
| $PQ_2$-26 | 3.8 | 44.2 | 15.6 | 19 | 14.4 |
| $PQ_2$-27 | 3.8 | 44.2 | 15.6 | 19 | 14.4 |
| $PQ_2$-28 | 4 | 45.3 | 13.8 | 20.5 | 16.3 |
| $PQ_{223}$-7 | 5.5 | 40.8 | 4.1 | 28.2 | 20.3 |
| $PQ_{223}$-8 | 5.4 | 38.1 | 3.9 | 29.5 | 22.1 |
| $PQ_{223}$-9 | 5.4 | 36.7 | 5.4 | 28.8 | 22.7 |

According to the invention, a preferred extract, CVT-E002, has a total carbohydrate content which comprises about 0.5-5 mol % rhamnose and/or about 11-22 mol % galacturonic acid and/or about 40-60 mol % glucose and/or about 10-19 mol % galactose and/or about 11-19 mol % arabinose. Preferably, CVT-E002 has a total carbohydrate content which comprises about 1-3 mol % rhamnose and/or about 13-20 mol % galacturonic acid and/or about 42-57 mol % glucose and/or about 12-17 mol % galactose and/or about 13-17 mol % arabinose. As indicated by the "and/or" terminology, the presence of the disclosed range for all of these monosaccharides is not critical. Therefore, one or more of these monosaccharides (preferably no more than two) can be outside of the disclosed range without affecting the utility of the extract.

A preferred extract, $PQ_2$, has a total carbohydrate content which comprises about 2-6 mol % rhamnose and/or about 41-49 mol % galacturonic acid and/or about 12-18 mol % glucose and/or about 16-22 mol % galactose and/or about 12-19 mol % arabinose. Preferably, $PQ_2$ has a total carbohydrate content which comprises about 3-5 mol % rhamnose and/or about 43-47 mol % galacturonic acid and/or about 14-16 mol % glucose and/or about 18-20 mol % galactose and/or about 14-17 mol % arabinose. Most preferably, $PQ_2$ has a total carbohydrate content which comprises about 4 mol % rhamnose and/or about 45 mol % galacturonic acid and/or about 15 mol % glucose and/or about 19 mol % galactose and/or about 15 mol % arabinose. As with CVT-E002, the presence of the disclosed range for all of these monosaccharides is not critical. Therefore, one or more of these monosaccharides (preferably no more than two) can be outside of the disclosed range without affecting the utility of the extract.

A preferred extract, $PQ_{223}$, has a total carbohydrate content which comprises about 3-8 mol % rhamnose and/or about 36-44 mol % galacturonic acid and/or about 2-7 mol % glucose and/or about 25-33 mol % galactose and/or about 17-25 mol % arabinose. Preferably, $PQ_{223}$ has a total carbohydrate content which comprises about 4-7 mol % rhamnose and/or about 37-42 mol % galacturonic acid and/or about 3-6 mol % glucose and/or about 27-32 mol % galactose and/or about 19-24 mol % arabinose. Most preferably, $PQ_{223}$ has a total carbohydrate content which comprises about 5 mol % rhamnose and/or about 39 mol % galacturonic acid and/or about 4 mol % glucose and/or about 29 mol % galactose and/or about 21 mol % arabinose. As with CVT-E002 and $PQ_2$, the presence of the disclosed range for all of these monosaccharides is not critical. Therefore, one or more of these monosaccharides (preferably no more than two) can be outside of the disclosed range without affecting the utility of the extract.

The extracts of the invention may be administered to a warm blooded mammal in need of treatment for autoimmune diseases, by intravenous, parenteral, topical, oral or rectal administration or by inhalation. The extract may be formulated for dosage by combining the extract with a conventional vehicle, excipient, binder, preservative, stabilizer, color, agent or the like as called for by accepted pharmaceutical practice in the form of tablets, capsules, liquids, lozenges, lotions or suppositories. Daily dosages are in the range of 0.1 mg to 5000 mg per kg of body weight, in between 1 and 10 daily doses, preferably between 0.5 mg to 70 mg per kg of body weight. Dosages depend on the activity of the specific compound, the age, weight, sex and conditions of the subjects to be treated, the type and severity of the disease, the frequency and route of administration, etc. Suitable dosages would be ascertained by those of skill in the art without undue experimentation. The extracts can also be combined with drugs or any other natural substances known to be effective for treating the condition in question.

The invention will now be further elucidated by the following Examples, which shows the effectiveness of the present invention.

Population: The study population were 37 members of a professional hockey club, the Edmonton Oilers team and organization. These individuals were, where possible, randomized into two groups: those that took CVT-E002 during the experimental period and those that did not (groups of 18 and 19, respectively). Some individuals (six in the control group and four in the CVT-E002 group) were vaccinated with a combination influenza strains A/Beijing, A/Sydney and B/Harbin between October 20 and Oct. 30, 1998.

Sampling Protocol: A preliminary blood sample (group A) was taken on Sep. 28, 1998, followed by a month during which individuals consistently took or did not take CVT-E002 (two tablets per day with very good compliance) then a second blood sample (group B) was taken between October 27 and Nov. 3, 1998. Both blood samples were immediately cultured (see below for analysis protocol).

Analysis Protocol: Peripheral blood leukocyte (PBL) suspensions were prepared by one step density centrifugation as previously described (McElhaney et al, Vaccine 14: 539-544 (1996)). This separates red blood cells and neutrophils from PBL that comprise monocytes, lymphocytes and other white blood cells (such as circulating dendritic cells). PBL were suspended at $1.5 \times 10^6$ per ml in RPMI, 10% fetal bovine serum and cultured with or without live influenza virus (three different strains—B/Harbin, A/Johannesberg, A/Nanchang) for a total of four different cultures on each sample). Culture supernatants and cells were collected after 2.5 and six days of culture. Serum from the original samples were assessed for total Ig concentrations by ELISA as described below.

Supernatant concentrations of IL-2 was measured by bioassay and cell lysate levels of Gr.-B by specific cysteine aspartase cleavage of the substrate t-butyloxycarbonyl-Ala-Ala-Asp-4-nitroanaline as previously described (McElhaney et al., supra). IL-10, IL-12, IFN-γ and TNF-α from culture supernatants were measured by ELISA as previously described (McElhaney et al., supra). Concentration was calculated relative to simultaneously run standard curves and expressed as ng/ml (IL-10, IL-12, IFN-γ and TNF-α) or units/ml (IL-2) culture supernatant or ASPase activity units/mg protein (GrB).

Where greater than half of the culture samples contained levels of a cytokine below assay detection limits, the analysis of that cytokine was eliminated. This excluded IL-12 production from the analysis. Where levels of other products were (rarely) below detection limit, the levels were set at the detection limit of the assay rather than zero. Missing a blood sample at the end of the study (October 28-November 3) eliminated an individual from the study. When too few cells were available for a complete analysis, not all assays were carried out. All the analyses were carried out on paired studies; thus, if an assay was not available from the second blood draw (the B sample), the corresponding A sample was also excluded.

Serum Ig levels were measured by ELISA method.

Both non-parametric (Mann-Whitney) and parametric (ANOVA) statistical analysis was carried out on the base concentration data. Since individuals express very different levels of the above cytokines and Gr.-B, the data was analyzed, and the statistics applied, in terms of the ratio of concentrations generated in cultures of PBL from the end (B=the second blood draw=October 27-November 3 group) and the start (A=the first blood draw=the September 28 group) of the study (the B/A ratio). Significance is given in terms of P-values, where 0.05 is considered significant.

The level of immunoglobulin (Ig) in the blood samples before and after treatment were directly measured. Culture supernatant levels of IL-12, IL-10, IL-2, IFN-γ, TNF-α and lysate Gr-B levels were determined for the four culture configurations (three different viruses and no antigen controls) on all PBL samples. Based on the fraction of 'below detection' assays, IL-12 production was excluded from the study. The ratio of cytokine or Gr-B levels before to after the one-month treatment period (B/A ratios) were calculated for each individual and for each culture treatment (four ratios per person). These ratios were then compared statistically as described above. The results are summarized for each cytokine/Gr-B below.

In order to estimate antigen-dependent production of cytokines or GrB, the fraction (F) of production in the presence of virus (V) minus production without virus (W) divided by production in the presence of virus was calculated [F=(V−W)/V]. This fraction is shown in FIG. 1 for pooled groups (treatment and control groups combined) for the four products (GrB, IFN-γ, IL10 and TNF-α) split into the start (A) and end (B) subgroups. The results suggest that 65%-95% of cytokine production is antigen-specific but that less than 30% of GrB production is antigen specific. The antigen-dependent fraction remained rather constant between the two blood samples.

The results are summarized in the following Tables, with discussion to follow.

TABLE 3

ANOVA Analysis of Combined Data Showing P Values for Production of Different Cytokines or GrB

| | P Value for Difference With: | |
| --- | --- | --- |
| Product | CVT-E002 (Cold-Fx) | Antigen (Virus) |
| Granzyme-B (combined) | 0.016 | 0.68 |
| TNF-α (combined) | 0.992 | 0.148 |
| TNF-α (non-vacc.) | 0.861 | 0.046 |
| IL-10 (combined) | 0.267 | 0.015 |
| IFN-γ (combined) | 0.177 | 0.736 |
| IL-2 (combined) | 0.286 | 0.413 |
| IL-2 (non-vacc.) | 0.238 | 0.197 |
| Ig (combined) | 0.122 | Not Applicable |
| Ig (non-vacc.) | 0.140 | Not Applicable |

TABLE 4

Mann-Whitney Analysis of the Effects of
CVT-E002 (Cold-Fx) on Before/After Production Ratios

| Immun-ologic Parameter | Significance (P Value) for Groups With the Following Inclusions: | | | | |
|---|---|---|---|---|---|
| | All Groups[1,2] | Non-vacc. only[2] | Virus cultures[2] | Virus cultures, non-vacc.[2] | Harbin only[1] |
| GrB | 0.012 | 0.025 | 0.0068 | 0.021 | 0.021 |
| TNF-α | 0.106 | 0.041 | 0.0069 | 0.0007 | 0.028 |
| IL-10 | 0.963 | 0.669 | 0.778 | 0.482 | 0.105 |
| IFN-γ | 0.269 | 0.475 | 0.311 | 0.624 | 0.165 |
| IL-2 | 0.120 | 0.023 | 0.110 | 0.027 | 0.888 |
| Ig | 0.192 | 0.140 | NA | NA | NA |

[1]B/A ratios ± SD for +Cold-Fx and -Cold-Fx groups bar graphed in FIG. 2.
[2]B/A ratios ± SD for +Cold-Fx and -Cold-Fx groups bar graphed in FIG. 3.
NA = not applicable.

Granzyme-B production: The above Tables split the data two ways (by antigen and whether individuals took CVT-E002) or three ways (by antigen and whether individuals took CVT-E002 or were vaccinated). 55 culture samples (out of a total of 148) were omitted from the analysis.

Table 3 shows the ANOVA analysis of ratios with post hoc t tests. It indicates that B/A ratio of Gr-B production with and without CVT-E002 were significantly different (P=0.016) but that the ratio was unaffected by presence or absence of antigen (P=0.68). FIG. 2 shows the B/A ratios with and without CVT-E002 (Cold-Fx) for all culture protocols (everything pooled="Total") and for each of the antigens and for the control (="None"). Note that all culture groups from the CVT-E002 treated group show a decrease in Gr-B production. Scheffe post hoc analysis with a significance level of 5% shows a decrease in the B/A ratio due to CVT-E002 treatment to be 0.246 with a P-value of 0.0147. Unpaired t-test analysis shows that CVT-E002 significantly decreased the B/A ratio for all culture groups combined (P=0.013) and for the Harbin virus antigen alone (P=0.036) but did not significantly affect the B/A ratios for all others, including the control group.

Mann-Whitney analysis (summarized in Table 4) also showed B/A ratios to be significantly different in the pooled analysis (P=0.012) and pooled analysis with vaccinated individuals removed (P=0.025), but that CVT-E002 did not significantly affect pooled B/A ratios for vaccinated individuals (P=0.215). Mann-Whitney analysis also showed that CVT-E002 very significantly decreased antigen-specific pooled B/A ratios (P=0.0068) as well as production in the presence of virus, non-vaccinated ratios (P=0.021). Mann-Whitney analysis confirmed unpaired t testing in showing that CVT-E002 significantly decreased only the B/A ratios for the Harbin antigen cultures both pooled (P=0.021) and non-vaccinated (P=0.021). FIG. 3 compares the B/A ratios for paired −CVT-E002 and +CVT-E002 groups for pooled cultures, vaccinated removed, no antigen removed, and both no antigen and vaccinated removed for visual comparison to the Mann-Whitney analysis shown in Table 4.

Production of TNF-α The descriptive statistics for data from day 2.5 of culture are summarized in the above Tables where the data is split two ways (by antigen and whether individuals took CVT-E002) or three ways (by antigen and whether individuals took CVT-E002 or were vaccinated). 48 samples (out of a total of 152) were omitted from the analysis.

Table 3 shows both the ANOVA analysis of ratios for all samples and the same analysis with vaccinated individuals removed. These data show that TNF-α production with and without CVT-E002 were not significantly different (P=0.992 or 0.861) but that there was a significant effect of antigen on B/A ratios in the non-vaccinated group (P=0.046). FIG. 2 shows the B/A ratios with and without CVT-E002 for all culture protocols, for each of the antigens and for the control (="None"). The significant effect of antigen on B/A ratios derives from all antigen-containing culture groups showing an increase due to CVT-E002 treatment but decrease in the B/A ratio in the antigen-independent culture group. Scheffe post analysis of pooled groups with a significance level of 5% shows a decrease in the B/A ratio due to CVT-E002 treatment to be 0.531 with a P-value of 0.695. Unpaired t-test analysis shows that CVT-E002 non-significantly decreased the B/A ratio for all culture groups combined (P=0.843) but approached significance only for the Nanchang virus antigen alone (P=0.079) and did not significantly affect the B/A ratios for all others, including the control group. Unpaired t-test analysis of the effect of CVT-E002 on B/A ratios when corrected for vaccination shows P values for the non-vaccinated groups to be always lower but that only the non-vaccinated Harbin culture group to be significant (P=0.044). Mann-Whitney analysis (Table 4) also showed B/A ratios to be non-significantly different in the pooled analysis (P=0.106) and pooled analysis with vaccinated individuals (P=0.811), but that CVT-E002 significantly decreased pooled B/A ratios for non-vaccinated individuals (P=0.041). In contrast, Mann-Whitney analysis showed that CVT-E002 very significantly increased pooled B/A ratios in virus-containing cultures considered as a pool separately (P=0.0069) as well as these cultures with the vaccinated group excluded (P=0.0007). Mann-Whitney analysis confirmed unpaired t testing in showing that CVT-E002 significantly increased the B/A ratios for the Harbin antigen cultures both pooled (P=0.028) and non-vaccinated (P=0.028) but also showed a significant effect of CVT-E002 on Johannesberg virus-treated cultures (P=0.029). FIG. 3 compares the B/A ratios for paired −CVT-E002 and +CVT-E002 groups for pooled cultures, vaccinated removed, no antigen removed, and both no antigen and vaccinated removed for visual comparison to the Mann-Whitney analysis shown in Table 4.

IL-10 production: The descriptive statistics are summarized in the above Tables that split the data two ways (by antigen and whether individuals took CVT-E002) or three ways (by antigen and whether individuals took CVT-E002 or were vaccinated). 55 culture samples (out of a total of 148) were omitted from the analysis.

Table 3 shows ANOVA analysis of ratios. It indicates that B/A ratio of IL-10 production with and without CVT-E002 were not significantly different (P=0.267), but that there was a significant effect of antigen on B/A ratios in the combined (vaccinated plus non-vaccinated) group (P=0.015). FIG. 2 shows the B/A ratios with and without CVT-E002 for all culture protocols and for each of the antigens and for the control (="None"). Note that the B/A ratios of two of three virus-containing culture groups were increased by CVT-E002 and one (J'berg) decreased. Antigen-independent B/A ratios were much larger than increases in virus-containing cultures (explaining the significant effect of antigen on B/A ratios) and the effect of CVT-E002 was a very large increase. Scheffe post hoc analysis with a significance level of 5% shows a seven-fold increase in the B/A ratio due to CVT-E002 treatment with a P-value of 0.233. Unpaired t-test analysis also shows that CVT-E002 non-significantly increased the B/A ratio for all culture groups combined (P=0.260) and did not significantly affect the B/A ratios for any individual group. Mann-Whitney analysis (Table 4) also showed B/A ratios to be non-significantly affected by CVT-E002 in the pooled analysis (P=0.963), pooled analysis with vaccinated individuals removed (P=0.669) or analysis with vaccinated individuals removed and only responses in virus-containing cultures included. FIG. 3 compares the B/A ratios for paired −CVT-E002 and +CVT-E002 groups for pooled cultures, vaccinated removed, no antigen removed, and both no antigen and vaccinated removed for visual comparison to the Mann-Whitney analysis shown in Table 4.

IFN-γ Production: The descriptive statistics are summarized in the above Tables that split the data two ways (by antigen and whether individuals took CVT-E002) or three ways (by antigen and whether individuals took CVT-E002 or were vaccinated). 55 culture samples (out of a total of 148) were omitted from the analysis.

Table 3 shows ANOVA analysis of ratios. It indicates that B/A ratio of IFN-γ production with and without CVT-E002 were not significantly different (P=0.177) and that there was not a significant effect of antigen on B/A ratios in the combined (vaccinated plus non-vaccinated) group (P=0.736). FIG. 2 shows the B/A ratios with and without CVT-E002 for all culture protocols and for each of the antigens and for the control (="None"). Note that the B/A ratios of all three virus-containing culture groups were decreased by CVT-E002 and that antigen-independent B/A ratios were essentially unchanged. Scheffe post hoc analysis with a significance level of 5% shows a 0.36 fold decrease in the B/A ratio due to CVT-E002 treatment with a P-value of 0.16. Unpaired t-test analysis also shows that CVT-E002 non-significantly decreased the B/A ratio for all culture groups combined (P=0.152) but approached significance for the Harbin group (P=0.098). Mann-Whitney analysis (Table 4) also showed B/A ratios to be non-significantly affected by CVT-E002 in the pooled analysis (P=0.269), pooled analysis with vaccinated individuals removed (P=0.475) or analysis with vaccinated individuals removed and only antigen-specific responses included. FIG. 3 compares the B/A ratios for paired −CVT-E002 and +CVT-E002 groups for pooled cultures, vaccinated removed, no antigen removed, and both no antigen and vaccinated removed for visual comparison to the Mann-Whitney analysis shown in Table 4.

IL-2 Production: The descriptive statistics are summarized in the above Tables that split the data two ways (by antigen and whether individuals took CVT-E002) or three ways (by antigen and whether individuals took CVT-E002 or were vaccinated). 48 culture samples (out of a total of 152) were omitted from the analysis.

Table 3 shows ANOVA analysis of ratios. It indicates that B/A ratio of IL-2 production with and without CVT-E002 were not significantly different (P=0.286) and that there was not a significant effect of antigen on B/A ratios in the combined (vaccinated plus non-vaccinated) group (P=0.413). FIG. 2 shows the B/A ratios with and without CVT-E002 for all culture protocols and for each of the antigens and for the control (="None"). Note that the B/A ratios of two of the virus-containing culture groups were increased by CVT-E002 and one decreased. Antigen-independent B/A ratios were essentially unchanged. Mann-Whitney analysis (Table 4) also showed B/A ratios to be non-significantly affected by CVT-E002 in the pooled analysis (P=0.120). However, Mann-Whitney analysis of the non-vaccinated group shows CVT-E002 to significantly decrease B/A ratios (P=0.023), but to significantly increase ratios in the non-vaccinated, virus-challenged group (P=0.027). FIG. 3 compares the B/A ratios for paired −CVT-E002 and +CVT-E002 groups for pooled cultures, vaccinated removed, no antigen removed, and both no antigen and vaccinated removed for visual comparison to the Mann-Whitney analysis shown in Table 4.

Blood sample Ig concentrations: The level of immunoglobulin (Ig) in the blood samples before and after treatment were directly measured. CVT-E002 increases serum Ig levels, although the effect is not significant (FIG. 2). ANOVA analysis of the effects of CVT-E002 in the combined and non-vaccinated groups (Table 3) shows a lack of significance (P=0.122 and 0.140, respectively). Mann-Whitney analysis (Table 4) also show non-significance (P=0.192 and 0.140, respectively).

The significant findings show that CVT-E002 treatment generally increased B/A ratios for IL-10 production and Ig levels (TH2 response indicators) and decreased B/A ratios for GrB and IFN-γ production (TH1 indicators). These results suggest that CVT-E002 is an excellent treatment for cell-mediated auto-immune diseases (e.g, auto-immune diabetes, Crohn's Disease, MS, early Rheumatoid Arthritis (RA)). Other complications such as in utero transmission of CMV and toxoplasma and pregnancy-induced hypertension (pre-eclampsia) have also been linked to aberrant TH1 responses. The type of moderate TH1 to TH2 shift that CVT-E002 appears to achieve is quite similar to the shift observed in pregnancy (although in pregnancy, antigen-specific TNF-α responses are also suppressed). RA goes into remission during pregnancy and flares after parturition, when the TH1/TH2 ratio returns to the pre-pregnancy balance.

We claim:

1. A method of decreasing granzyme B in a patient in need thereof, the method comprising administering an effective amount of CVT-E002 to said patient, wherein CVT-E002 is an extract fraction of ginseng prepared by a method comprising the following steps:

a) combining American ginseng with a first solvent comprising an alcohol in a proportion of about 7-9 ml of said first solvent per gram of ginseng and heating the resulting solution at a temperature of about 80-100° C. for a time period of about 2-4 hours, to produce a first ginseng solution;

b) separating the first ginseng solution to produce an alcohol ginseng solution and a first ginseng residue;

c) combining the first ginseng residue with water in a proportion of about 7-9 ml of water per gram of ginseng residue and heating the ginseng residue solution at a temperature of about 80-100° C. for a time period of about 2-4 hours, to produce a ginseng residue solution;

d) separating the ginseng residue solution to produce a second ginseng residue and an aqueous extract solution containing a ginseng extract; and e) drying or concentrating the aqueous extract solution of part (d) to produce ginseng fraction CVT-E002.

* * * * *